United States Patent [19]
Levy

[11] Patent Number: 5,327,477
[45] Date of Patent: Jul. 5, 1994

[54] FILM POSITIONING SYSTEM FOR DENTAL X-RAY PROCEDURES

[76] Inventor: Paul Levy, 625 Main St., #19, Reading, Mass. 01867

[21] Appl. No.: 977,616

[22] Filed: Dec. 29, 1992

[51] Int. Cl.⁵ .............................................. A61B 6/14
[52] U.S. Cl. .................................. 378/168; 378/170; 378/205
[58] Field of Search ............... 378/68, 167, 168, 169, 378/170, 177, 205

[56] References Cited

U.S. PATENT DOCUMENTS

| | | |
|---|---|---|
| 4,554,676 | 11/1985 | Maldonado et al. ............... 378/170 |
| 4,949,370 | 8/1990 | Tanaka ............................... 378/170 |

*Primary Examiner*—David P. Porta
*Attorney, Agent, or Firm*—Joseph S. Iandiorio; Kirk Teska

[57] ABSTRACT

A film positioning system for dental X-ray procedures including a plurality of film carriers each including a film holder on one end and an attachment rod extending therefrom; and an X-ray tube aiming device including a plurality of distinct attachment rod holders for separately positioning each film carrier in the proper orientation with respect to the X-ray tube.

13 Claims, 3 Drawing Sheets

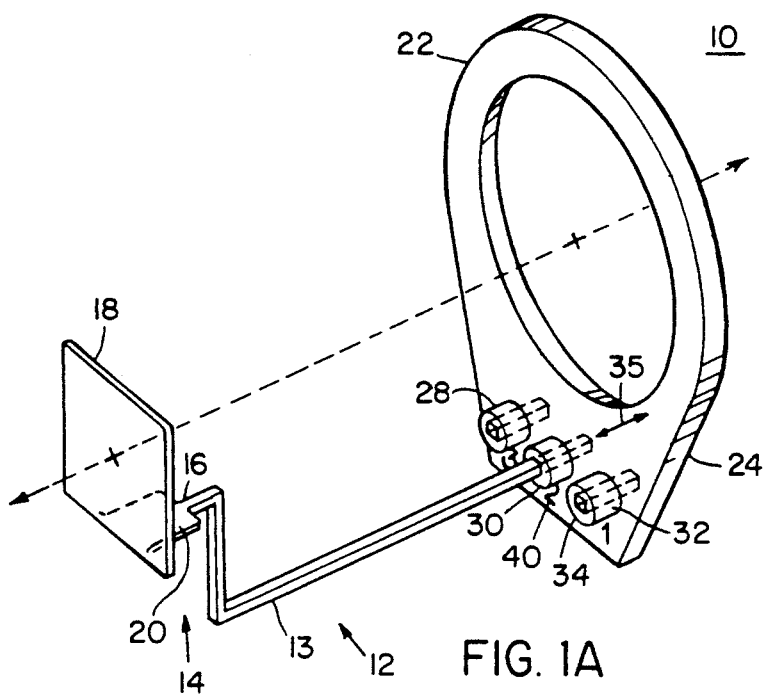
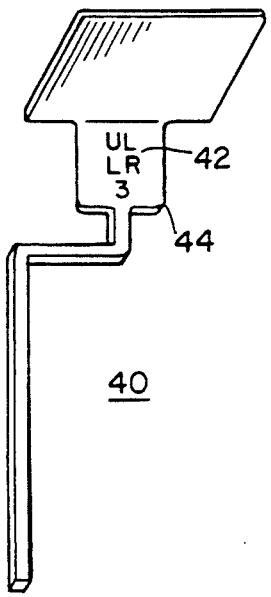
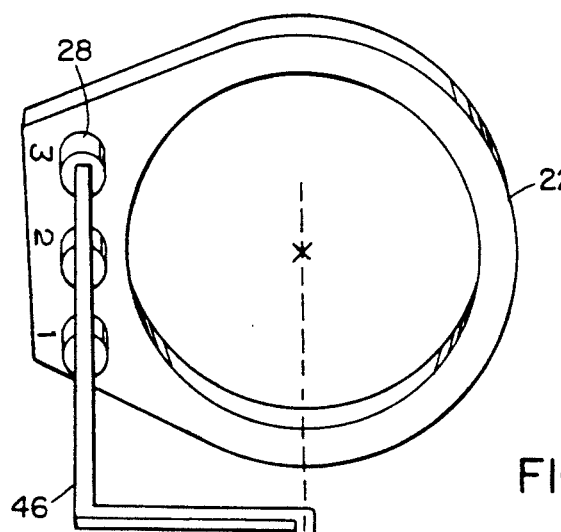
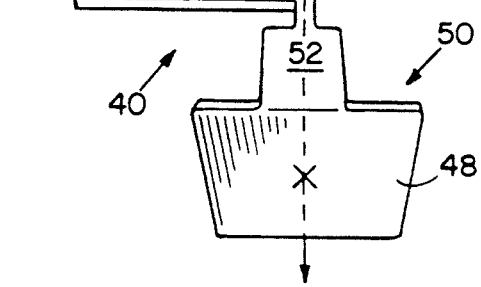
FIG. 1A
FIG. 1B
FIG. 1C

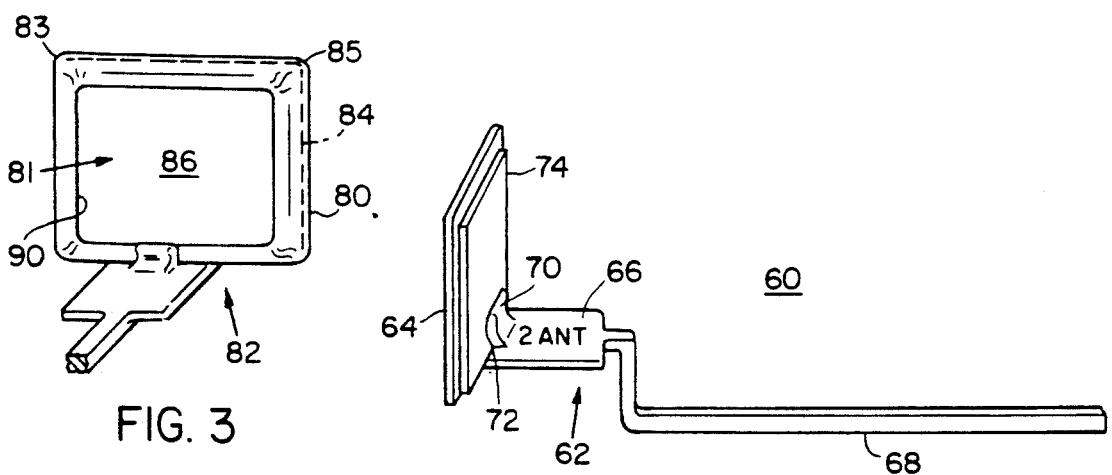
FIG. 3
FIG. 2
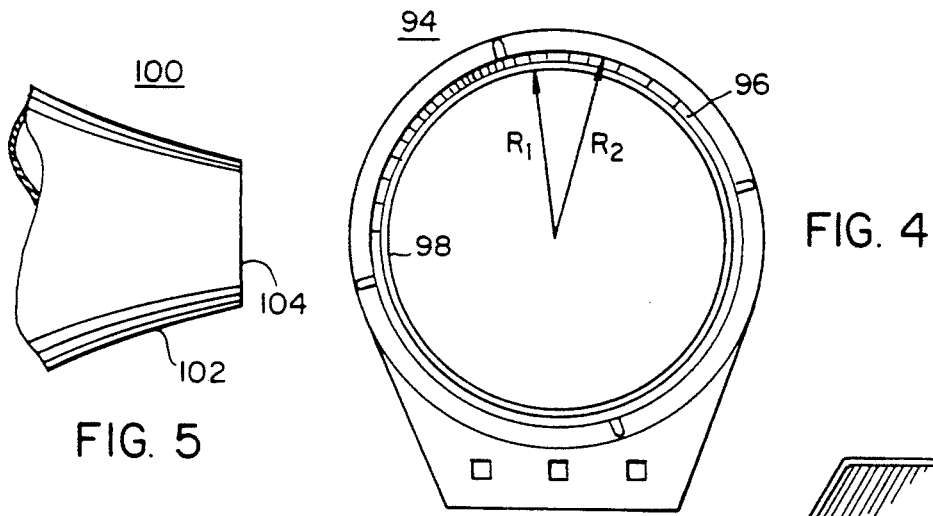
FIG. 5
FIG. 4
FIG. 6
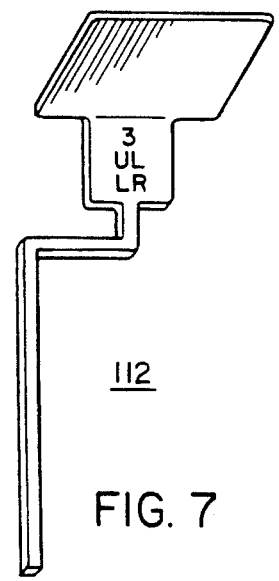
FIG. 7

FILM POSITIONING SYSTEM FOR DENTAL X-RAY PROCEDURES

FIELD OF INVENTION

This invention relates to a film positioning system for dental X-ray procedures which assures a fixed relationship between the X-ray equipment and the X-ray film and which also assures individual film holders are properly positioned in the patient's mouth with respect to the X-ray equipment.

BACKGROUND OF INVENTION

Dental radiographs are made using X-ray examination units suited for dental purposes. Dental X-ray films have been developed for intraoral shots and generally have a plate-like construction and standardized dimensions so that the film can be introduced into the oral cavity.

In one procedure, the film alone is placed within the patient's mouth and held in place proximate the tooth or teeth to be filmed when the patient closes her mouth over the film. It has been determined, however, that proper orientation of the film with respect to the tooth or teeth to be filmed, for example, parallel to the longitudinal axis of the tooth, is required to eliminate distortions, improper focus, and the like.

Therefore, film carriers are used including a back plate for mounting the X-ray film and a bite plate orientated at a right angle to the back plate. The X-ray film is held against the back plate, the film carrier is introduced at the proper location within the patient's mouth, and the patient is instructed to bit down on the bite plate.

There is still a need, however, to assure proper orientation of the X-ray tube with respect to the X-ray film mounted against the back plate. Hence, Furhrmann (U.S. Pat. No. 4,965,885) teaches a film carrier capable of engaging with one end of a guide rod at different locations on the film carrier by means of a plurality of spaced bores in the bite plate. The other end of the connecting rod is slideably received through an orifice in a sighting ring affixed circumferentially around the X-ray cone. The U.S. Pat. Nos. to Updegrave (3,745,344) and Levy (1,947,014) teach similar constructions.

One problem with such constructions, however, is that the X-ray technician is still left with the task of assuring proper a orientation of the film carrier within the patient's mouth and also a proper orientation between the film carrier and the aiming ring. X-ray technicians, although skilled, may not always be able to assure proper orientation of the film carrier in the patient's mouth or proper orientation of the film carrier with respect to the aiming ring as it presently has been constructed in prior art devices.

In prior art devices such as Furhrmann, two positioning procedures must be performed. First, the guide rod must be placed in the proper bore in the biting plate; second, the guide rod must be properly positioned within the aiming ring to assure the correct distance between the X-ray cone and the film. If the doctor orders X-rays of the upper right, lower left and anterior portions of the patient's mouth, it may not always be readily apparent to the technician which arrangements and configurations are proper for best filming. Worst, once the proper adjustments are made, realignment may be needed if the patient moves his head or the guide rod improperly moves with respect to the aiming ring. Improper film orientation resulting from the use of such devices is inefficient, results in unnecessary radiation exposure, and patient discomfort. The technician may not be aware of movement resulting in improper exposures, and the need for additional X-rays may not be known until the X-ray plates are exposed.

Another, related problem is that prior art devices may require a separate uniquely configured aiming ring for each film holder. This adds to the overall expense of prior art systems, and also increases the possibility of confusion in matching the correct film holder with the correct aiming ring.

SUMMARY OF INVENTION

It is therefore an object of this invention to provide a film positioning system and method for dental X-ray procedures which secures the film in a defined and more accurate position thereby facilitating more accurate X-rays.

It is a further object of this invention to provide such a film positioning system and method which is easier to use than current available systems.

It is a further object of this invention to provide such a film positioning system and method which does not include numerous moving parts thereby resulting in more stable dental X-ray procedures.

It is a further object of this invention to provide such a film positioning system and method which is more stable thereby eliminating unnecessary radiation exposure, and patient discomfort.

It is a further object of this invention to provide such a film positioning system and method which eliminates movement between the X-ray source and the X-ray film located within the patient'mouth thereby producing more accurate results.

It is a further object of this invention to provide such a film positioning system and method which facilitates exposure of all four corners of the X-ray film.

It is a further object of this invention to provide such a film positioning system and method which includes a comfortable cushion cover that may be reused for the entire series of X-rays for the same patient.

It is a further object of this invention to provide such a film positioning system and method which facilitates the use of disposable bite blocks thwarting the spread of infection and communicable diseases.

It is a further object of this invention to provide such a film positioning system and method which is generally more comfortable to the patient.

It is a further object of this invention to provide such a film positioning system and which is cost efficient to manufacture; in which the bite blocks are autoclavable; and includes disposable covers.

This invention results from the realization that a fixed relationship between the X-ray film and the portion of the patient's mouth to be X-ray, and between the X-ray equipment and the X-ray film, can be achieved with a single aiming ring which accepts a number of uniquely configured film holders automatically insuring the proper positioning of each film holder in the patient's mouth and with respect to the X-ray equipment; and furthermore that the guess work of determining proper film holder orientation can be eliminated by distinct film holder recepticals on the aiming ring each annotated for association with its corresponding film holer thereby eliminating the need for complicated adjustments, separate aiming rings for each film holder, and film movement resulting in retakes and unnecessary radiation exposure.

This invention features a film positioning system for dental X-ray procedures in which a plurality of film carriers each including film holder means on one end and an attachment rod extending therefrom are uniquely mated with a plurality of distinct positioning means on an X-ray tube aiming device for separately positioning each film carrier in the proper orientation with respect to the X-ray tube. Each film carrier may include a uniquely shaped attachment rod configured for association with at least one distinct positioning means such as an attachement rod holder for assuring proper orientation of the film holder within the patient's mouth. There may also be means for assuring each uniquely shaped attachment rod as correctly associated with its corresponding attachment rod holder such as annotations on each film carrier and complementary annotations proximate each distinct attachment rod holder. Each attachment rod holder may include a receptacle for receiving its corresponding attachment rod and may also include an orifice therethrough for longitudinal adjustment of its corresponding film carrier with respect to the uniquely single aiming device.

Each film holder means may include a film support plate receivable within the patient's mouth for positioning the X-ray film, and means for releasably securing the film against the support plate such as a frictional support member biased with respect to the film support plate for releasably receiving the X-ray film by means of a frictional fit between the frictional support member and the film support plate. The aiming device my include a circumferential aiming ring having a uniquely beveled interior surface for a secure releasable engagement of the aiming ring on the X-ray tube.

This invention also features a pliable sleeve for covering at least a portion of the film holder means for increased patient comfort and sanitation. The sleeve may be made of a thermoplastic material, have rounded edges for increased patient comfort, and may even be flavored.

This invention also features a film carrier positioning system for dental X-ray equipment including a plurality of film carriers each including a bit block on one end and an attachment rod extending therefrom, and film carrier orientation means removably affixable to the X-ray examining equipment including a plurality of distinct attachment rod holders each positioned for proper orientation of at least one bit block within the patient's mouth during the X-ray procedure. The film carrier orientation means may include an aiming ring for circumferential engagement with the X-ray aiming equipment. Each film carrier may be uniquely configured for engagement a corresponding distinct rod holder. Furthermore, there may be means for assuring each film carrier is mated with its corresponding attachment rod holder such as annotations on each film carrier and complementary annotations proximate each distinct attachment rod holder.

This invention also features a film positioning system for dental X-ray equipment including a plurality of uniquely configured film carriers each including a film support plate on one end and an attachment rod extending therefrom, each film carrier uniquely configured for filming a particular portion of the patient's mouth; and film carrier orientation means affixable to the X-ray equipment including a plurality of distinct attachment rod holders each positioned for automatic proper orientation of at least one of the film carriers with respect to a particular portion of the patient's mouth to be filmed; and at least one pliable sleeve for covering the film support plate.

Finally, this invention features a dental X-ray method for a film carrier positioning system including selecting, from a plurality of distinctly shaped film carriers each having a bite on the distal end thereof and an attachment rod extending therefrom, the proper film carrier for the set of teeth to be filmed; placing an X-ray film about the bite block; engaging the attachment rod of the selected film carrier with the positioning means of an aiming ring which includes distinct rod holders for assuring the proper orientation of the film carriers with respect to the X-ray tube; placing the bite block of the selected film carrier in the patient's mouth; and guiding the X-ray tube within the uniquely beveled aiming ring.

DISCLOSURE OF PREFERRED EMBODIMENT

Other objects, features and advantages will occur to those skilled in the art from the following description of a preferred embodiment and the accompanying drawings, in which:

FIG. 1A is a schematic diagram of an embodiment of the film positioning system of this invention;

FIG. 1B is a schematic diagram of an annotated film carrier of this invention;

FIG. 1C is a perspective view of the film carrier shown in FIG. 1B positioned in the aiming ring of FIG. 1A;

FIG. 2 is a more detailed side view of a film carrier of this invention showing frictional support means for holding the X-ray film about the support plate;

FIG. 3 is a perspective view of a sleeve placed about the film holder of this invention for increased patient comfort;

FIG. 4 is a rear view of one embodiment of the aiming ring of this invention;

FIG. 5 is a partial side view of a dental X-ray tube on which the aiming ring of FIG. 4 is placed during the X-ray procedure;

FIG. 6 is a side view of an anterior film carrier according to this invention;

FIG. 7 is a schematic diagram of a posterior upper left, lower right film carrier according to this invention;

Figure 8:
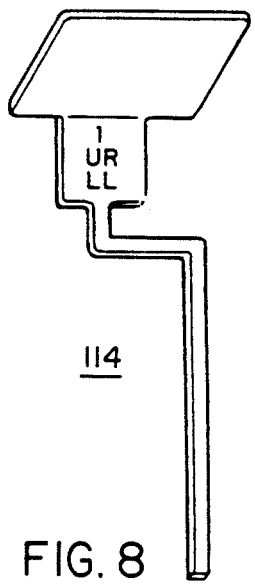
FIG. 8 is a schematic diagram of an upper right, lower left film carrier according to this invention.

X-ray film positioning system 10, FIG. 1A, includes film carrier 12, in this example a film carrier particularly configured for the anterior portion of the mouth. Bite block portion 14 located on distal end 16, includes film holder support plate 18 and biting surface 20. Attachment rod 13, extends from bite block 14 and is preconfigured for proper orientation of bite block 14 with respect to sighting ring 22. Sighting ring 22 is circumferentially engageable about an X-ray tube (not shown) and includes positioning means 24 for automatically positioning film carrier 12 in the proper orientation with respect to the line of sight of the X-ray cone shown by line 26. In this embodiment, positioning means 24 includes film carrier receptacles in the form of rod holders 28, 30, and 32 each including an orifice 34 therethrough shown in FIG. 1A with respect to rod holder 32. The attachment rod 13 passes slideably within rod holder 30 or even completely through as shown by arrow 34. Note that film carrier 12 is preconfigured such that when fit into holder 30, line of site 26 between the center of aiming ring 22 and the center of support plate 18 is such that proper orientation of the film (not shown) with respect to the teeth of interest and also proper orientation of the film with respect to the X-ray cone is assured. This configuration also helps in assuring all four corners of the X-ray film are exposed.

As noted, film carrier 12 is particularly suited to filming the anterior portion of the patient's mouth. In the position shown in FIG. 1A, the upper anterior may be filmed when the patient bites down on bite surface 20. In this orientation, film support plate 18 is proximate the upper teeth. Rotating aiming ring 180 degrees on the X-ray tube places film carrier 12 in the proper position for filming the lower anterior teeth.

Film carrier 40, FIG. 1B, however, is preconfigured for filming either the upper left or lower right posterior portions of the patient's mouth.

Therefore, according to this invention, there are a plurality of film carriers each configured such that when placed in the appropriate rod holders 28, 30, 32, FIG. 1A, the proper orientation of the film within the patient's mouth is assured. Moreover, to guarantee that the X-ray technician correctly places the correct film holder in the proper orientation with respect to positioning means 24 of aiming ring 22, each film holder is annotated as shown for film holder 40, FIG. 1B. The embossed or molded annotation 42 on bite plate 44 is "UL", and "LR", corresponding respectively to "upper right", and "lower left" filming within the patient's mouth. The "3" corresponds to rod holder 28, FIG. 1A which is also annotated with a "3" as shown at 46. Film holder 12 would have the annotation "2", "ANT" assuring that the technician uses film holder 12 for anterior shots and also that film holder 12 is properly placed in rod holder 30 which has a complementary annotation "2".

Therefore, the technician does not have to adjust the film holder with respect to aiming ring 22 for proper orientation and much of the guess work of dental radiography is eliminated. For example, if the dentist orders lower right posterior X-rays of the patient, the technician selects film carrier 40, FIG. 1B, notes the "LR" corresponding to lower right, and with the film in place against film support surface plate 48, FIG. 1C, bite block 50 is placed proximate the desired location on the right side of the patient's mouth. When the patient bites down on the biting surface 52, film support plate 48 is correctly and automatically positioned proximate the patient's lower teeth on the right side. Then, noting the annotation "3", the technician places attachment rod 46 in rod holder 28 also annotated with a "3". Aiming ring 22 is then slid onto the X-ray cone.

In this way, a more stable system is achieved insuring proper X-ray film alignment and system accuracy. Time is saved and patient comfort is increased because the numerous adjustments required in prior art systems are not required in the single ring film positioning system according to this invention. Moreover, there is a fixed relationship between the X-ray film and the portion of the patient's mouth to be filmed, and also uniquely to this invention, a precise orientation between the X-ray equipment and the X-ray film. A single aiming ring excepts a number of uniquely configured film holders thereby insuring the proper position of each film holder. The guess work of determining the proper orientation is eliminated by distinct film holder receptacles on the aiming ring each annotated for association with its corresponding film holder. Perhaps most importantly, film movement is reduced and retakes resulting in unnecessary radiation exposure are not required.

Film carrier 60, FIG. 2, generally includes film holder or bit block portion 62 having a film support plate 64 extending more or less perpendicularly from biting surface 66. Attachment rod 68 extends in a preconfigured pattern from bite block portion 62 as discussed above.

Frictional support member 70, located at the intersecting gap 72 between biting plate 66 and offset film support plate 64, releasably secures film 74 against film support plate 64 by means of a frictional fit within gap 72. This configuration also allows injection molding or similar manufacturing processes of film carrier 60 resulting in a preferred and cost efficient unitary configuration. Support member 70 is biased for releasably securing film 74 against support plate 64.

The system of this invention also includes sleeve 80, FIG. 3, for encompassing at least a portion of bite block 82, namely support plate 84 thereby assisting in keeping film 86 in the proper orientation on support plate 84. Sleeve 80 includes opening 90 which receives film support plate 84 and film 86. Opening 90 leads to inner cavity 81 which has width and depth dimensions approximately the same as those of X-ray film 86 so that film 86 fits snugly therein to hold the film in place and protect the patient from the generally sharp film edges.

Sleeve 80 further assists in greater X-ray fidelity by holding X-ray film 86 more firmly against support plate 84. Sleeve 80 also insures a more sanitary system since it can be economically disposed of after use on one patient. Moreover, sleeve 80 prevents the film from becoming wetted with saliva facilitating the film development process. In short, film 80 holds the X-ray film firmly and comfortably in place by encompassing the exposed edges of the film with a soft, pliable sleeve having an opening approximately the size of the film so the film can slide into the sleeve. Rounded edges 83 and 85 further increase patient comfort. In addition, sleeve 80 may be flavored. For example, a flavoring agent could be placed in close proximity to sleeve 80 during packaging and the favoring agent could leach onto sleeve 80. Alternatively, a flavoring agent could be added during manufacture of sleeve 80 for masking an otherwise plastic or rubber taste.

Aiming ring 94, FIG. 4, according to this invention includes a unique beveled interior surface 96 defining a radius $R_1$ at the rear of aiming ring 94 which faces the X-ray tube and a smaller radius $R_2$ at the front of aiming ring 94 which faces the patient. Ridge 98 in conjunction with beveled surface 96 insures a frictional fit of aiming ring 94 on X-ray tube 100, FIG. 5 which generally has a complementary configuration, namely sloping surface 102 having the smallest diameter at end 104 which is placed proximate the patient's mouth.

Although aiming ring 94 is shown having a circular shape which receives a tubeshaped X-ray head 100, FIG. 5, this is not a limitation of this invention. Aiming ring 94 could be square shaped or otherwise properly configured for temporary attachment to other known X-ray devices. Moreover, other film carrier positioning means affixable to the X-ray device including a plurality of distinct attachment rod holders are within the scope of this invention. Aiming ring 94 may be configured to circumferentially engage the most common X-ray tubes and then other adapters may be designed to affix aiming ring 94 to X-ray tubes of other configurations.

Figure 9:
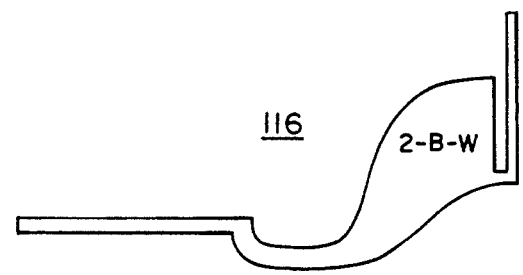
FIG. 9 is a side view of a bite-wing film carrier according to this invention.

To assure accurate and defined positioning of the X-ray film within the patient's mouth, the plurality of correctly positioned rod holders 28, 30, and 32, FIG. 1A, according to this invention allow the use of distinctly configured film carriers such as anterior film carrier 110, FIG. 6; posterior upper left and lower right film carrier 112, FIG. 7; posterior upper right and lower left film carrier 114, FIG. 8; and bite-wing film carrier 116, FIG. 9. Vertical bite-wing holders may also be included.

Figure 10:
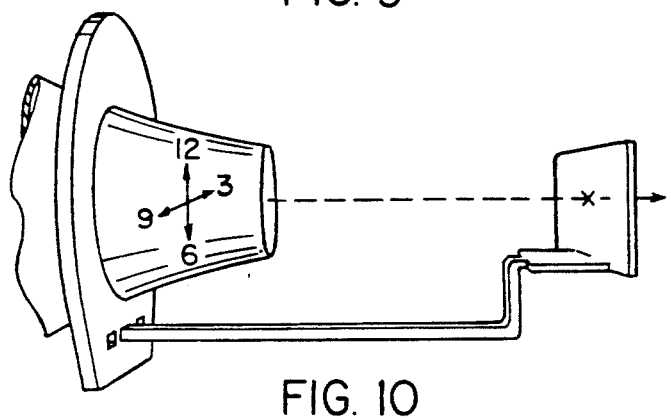
FIG. 10 is a perspective view of the film positioning system of this invention deployed on an X-ray cone in the proper orientation for filming the upper anterior teeth.

Anterior film carrier 110, FIG. 6, is correctly mated with rod holder 30, (position 2) FIG. 1A, of aiming ring 22 positioned on the X-ray tube such that rod holder 30 is proximate the 6 O'clock position for filming the upper anterior teeth as shown in FIG. 10. For filming the lower anterior teeth, rod holder 30 is positioned proximate the 12 O'clock position.

Posterior upper left and lower right film carrier 112, FIG. 7, is mated with rod holder 28, FIG. 1A (position 3) of aiming ring 22 positioned on the X-ray tube such that rod holder 28 is proximate the 9 O'clock position for filming the lower right teeth, and positioned proximate the 3 O'clock position for filming the upper left teeth. Posterior lower left and upper right film carrier 114, FIG. 8, is mated with rod holder 32, FIG. 1A, (position 1) of aiming ring 22 positioned on the X-ray tube such that rod holder 32 is proximate the 9 O'clock position for filming the upper right teeth and positioned in the 3 O'clock for filming the lower left teeth.

Figure 11:
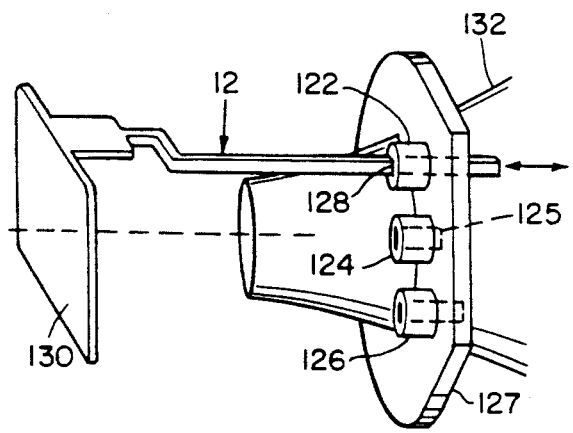
FIG. 11 is a perspective view of the film positioning system of this invention deployed on an X-ray cone in another position.

Although the positioning means discussed herein are related to rod holders 122, 124 and 126, FIG. 11, each having an orifice 128 as shown for rod holder 12 which allows for proper longitudinal positioning of film plate 130 with respect to X-ray tube 132, such an embodiment is not a limitation of the following claims and other embodiments will occur to those skilled in the art so long as there are positioning means for automatically positioning each film carrier in the proper orientation with respect to X-ray tube 132. Proper dimensioning of aiming ring 22, FIG. 1A, with respect to an X-ray tube 132 would automatically fix the proper distance between the X-ray tube lens and film support plate 130 further reducing the need for longitudinal adjustment. For example, film carrier rod holder 124 is shown having a cavity 125 which does not extend completely through aiming ring 127. And, instead of annotations as discussed above, each attachment rod could be uniquely configured for mating only with its correct corresponding rod holder as will be understood by those skilled in the art. This could be accomplished by using different shaped receptacles in the aiming ring corresponding with each rod. Hence means for assuring each attachment rod is correctly associated with its corresponding positioning means may include the embodiments described herein and equivalents.

Figure 12:
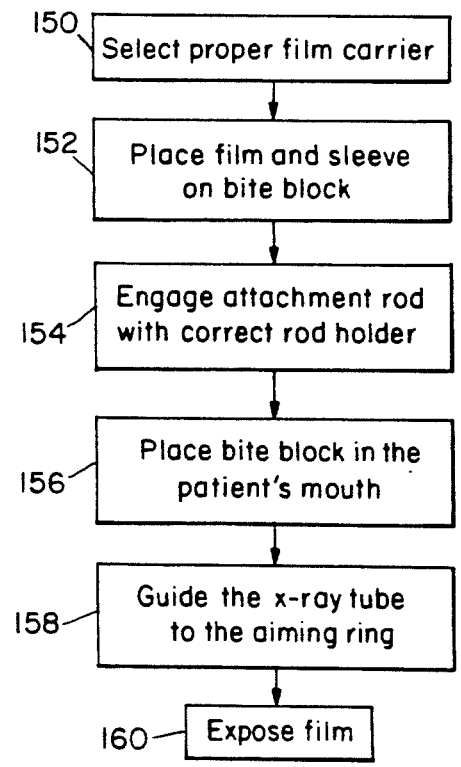
FIG. 12 is a flow diagram of the film positioning method according to this invention.

The method of utilizing the system of this invention, then, includes: first selecting the proper film carrier for the set of teeth to be filmed, step 150, FIG. 12. Next, the film is placed in its proper location of the bite block and the protective sleeve is placed around the film/bite block combination, step 152. The attachment rod is then fitted into the corresponding rod holder of the aiming ring, step 154 and the bite block is placed within the patient's mouth, step 156. The X-ray tube is guided to the aiming ring, step 158 and the film is exposed, step 160. In this way, the system and method of this invention assures first that the film does not move with respect to the film holder once placed in the patient's mouth and second that the X-ray tube is maintained in the proper position with respect to the patient's mouth and the film carrier for accuracy. As shown in FIG. 10, the system of this invention assures a fixed relationship between the X-ray tube and the film holder limiting radiation exposure, guaranteeing accuracy, and eliminating patient discomfort. Aiming ring 22, FIG. 1A, and film holders 40, FIG. 1; 110, FIG. 6; 112, FIG. 7; 114, FIG. 8; and 116, FIG. 9 may be made of the same thermoplastic or thermosetting materials or similar including polypropelene, manufactured fairly inexpensively by known extrusion, or injection, or autoclave methods, and sold as kits or separately. The film holders could be considered disposable for reduced disinfection costs and disease transmission. Sleeve 80, FIG. 3 may be vinyl or any soft pliable material such as thermoplastic rubber for increased patient comfort since the fairly sharp edges of the film do not come into contact with sensitive tissue. One material that has been successfully used for sleeve 80, possessing the softness and pliability desired so that the sleeve can stretch over the film and bite block combination is "Kraton" made by the Shell Chemical Company. It will be readily appreciated that sleeve 80 is also disposable for increased sanitation.

Although specific features of the invention are shown in some drawings and not others, this is for convenience only as some feature may be combined with any or all of the other features is accordance with the invention.

Other embodiments will occur to those skilled in the art and are within the following claims:

What is claimed is:

1. A film positioning system for dental X-ray procedures comprising:
    a plurality of film carriers each including film holder means on one end and a uniquely shaped attachment rod extending therefrom;
    an X-ray tube aiming device including a plurality of distinct positioning means for separately positioning each said film carrier in the proper orientation with respect to said X-ray tube; and
    means for assuring each said uniquely shaped attachment rod is correctly associated with its corresponding distinct positioning means including an annotation on each said film carrier and complementary annotations proximate each said distinct positioning means for assuring proper orientation of said film holder within the patient's mouth.

2. The film positioning system of claim 1 in which said plurality of distinct positioning means include spaced attachment rod holders each including a receptacle for receiving said attachment rods.

3. The film positioning system of claim 2 in which each said attachment rod holder includes an orifice for receiving a said attachment rod therethrough for longitudinal adjustment of said film carriers with respect to said aiming device.

4. The film positioning system of claim 1 in which each said film holder means includes a film support plate receivable within the patient's mouth for positioning the X-ray film.

5. The film positioning system of claim 4 in which each said film holder means further includes means for releasably securing the film against said film support plate.

6. The film positioning system of claim 5 in which each said means for releasably securing the film against said film support plate includes a frictional support member biased with respect to said film support plate for releasably receiving the X-ray film by means of a frictional fit between said frictional support member and said film support plate.

7. The film positioning system of claim 1 in which said aiming device includes a circumferential aiming ring having a beveled interior surface for secure releasable engagement of said aiming ring on the X-ray tube.

8. The film positioning system of claim 1 further including at least one pliable sleeve for covering at least a portion of said film holder means.

9. The film positioning system of claim 8 in which said sleeve is made of a thermoplastic material.

10. The film positioning system of claim 8 in which said sleeve has rounded edges for increase patient comfort.

11. The film positioning system of claim 8 in which said sleeve is flavored for increased patient comfort.

12. A film carrier positioning system for dental X-ray equipment comprising:
   a plurality of uniquely configured film carriers each including a bite block on one end and an attachment rod extending therefrom;
   film carrier orientation means removably affixable to the X-ray examining equipment including a plurality of distinct attachment rod holders each positioned for proper orientation of at least one said bite block within the patient's mouth during the X-ray procedure; and
   means for assuring each said film carrier is mated with its corresponding attachment rod holder including annotations on each said film carrier and complementary annotations proximate each said distinct attachment rod holder.

13. The film carrier positioning system of claim 12 in which said film carrier orientation means include an aiming ring for circumferential engagement with the X-ray examining equipment.

* * * * *